(12) United States Patent
Haines et al.

(10) Patent No.: US 9,937,015 B2
(45) Date of Patent: Apr. 10, 2018

(54) SURGICAL DRAPE CONFIGURED FOR PERIPHERALLY INSERTED CENTRAL CATHETER PROCEDURES

(75) Inventors: Kimberly Haines, Deerfield, IL (US); Lindsay S. Yakel, Baltimore, MD (US)

(73) Assignee: Medline Industries, Inc., Northfield, IL (US)

( * ) Notice: Subject to any disclaimer, the term of this patent is extended or adjusted under 35 U.S.C. 154(b) by 1467 days.

(21) Appl. No.: 13/229,743

(22) Filed: Sep. 11, 2011

(65) Prior Publication Data

US 2012/0298115 A1   Nov. 29, 2012

Related U.S. Application Data

(63) Continuation-in-part of application No. 13/116,473, filed on May 26, 2011, now Pat. No. 9,820,751.

(51) Int. Cl.
| | |
|---|---|
| *A61B 19/00* | (2006.01) |
| *A61F 5/37* | (2006.01) |
| *A61B 46/23* | (2016.01) |
| *A61B 46/00* | (2016.01) |
| *A61B 17/132* | (2006.01) |
| *A61B 17/00* | (2006.01) |
| *A61B 46/20* | (2016.01) |

(52) U.S. Cl.
CPC ............ *A61B 46/23* (2016.02); *A61B 46/00* (2016.02); *A61B 17/1322* (2013.01); *A61B 2017/00902* (2013.01); *A61B 2046/201* (2016.02)

(58) Field of Classification Search
CPC .................................................... A61B 19/08

USPC ................... 128/852, 853, 854, 849
See application file for complete search history.

(56) References Cited

U.S. PATENT DOCUMENTS

| | | | |
|---|---|---|---|
| 313,046 A | 3/1885 | Batdorf |
| 371,353 A | 10/1887 | Perry |
| 850,960 A | 4/1907 | O'Connoor |
| 1,506,332 A | 8/1924 | Bloom |

(Continued)

FOREIGN PATENT DOCUMENTS

| | | |
|---|---|---|
| DE | 8904426 | 5/1989 |
| DE | 202006005966 | 10/2006 |

(Continued)

OTHER PUBLICATIONS

Vanatta, Amy "Non-Final Office Action", U.S. Appl. No. 12/720,360, filed Mar. 9, 2010; dated Oct. 11, 2011.

(Continued)

*Primary Examiner* — Victoria J Hicks
(74) *Attorney, Agent, or Firm* — Philip H. Burrus, IV

(57) ABSTRACT

A medical drape includes a patient drape (100) and a radial drape attachment (200). The radial drape attachment can be coupled to the patient drape by way of an adhesive coupling (202). The radial drape attachment includes defines one or more fenestrations (205) or apertures through which a central line may be inserted. Some or all of the radial drape attachment (200)can be transparent or pellucid. Portions of the radial drape attachment can be opaque as well. A support layer can be configured to be absorptive, fluid impenetrable, or both. A tourniquet (1801) may be integrated with the radial drape attachment, as can one or more tool-less removal features (209). Pouches (901,902) can be added to catch fluids or hold medical implements during a procedure.

6 Claims, 11 Drawing Sheets

(56) References Cited

U.S. PATENT DOCUMENTS

| | | |
|---|---|---|
| 1,980,435 A | 11/1934 | Reagan |
| 2,172,162 A | 8/1939 | Gillette |
| 2,430,941 A | 11/1947 | Long |
| 2,653,324 A | 8/1953 | McMahon |
| 2,673,347 A | 3/1954 | Weiss |
| 2,825,902 A | 3/1958 | Breier |
| 3,144,661 A | 8/1964 | Buser |
| 3,276,036 A | 10/1966 | Carter et al. |
| 3,359,569 A | 12/1967 | Scrivens |
| 3,397,406 A | 8/1968 | Leach |
| 3,399,406 A | 9/1968 | Bradley |
| 3,429,433 A | 2/1969 | Holt |
| 3,451,062 A | 6/1969 | Bradley |
| 3,540,441 A | 11/1970 | Collins |
| 3,625,206 A | 12/1971 | Charnley |
| 3,696,443 A | 10/1972 | Taylor |
| 3,707,964 A | 1/1973 | Patience et al. |
| 3,721,999 A | 3/1973 | Goya et al. |
| 3,750,664 A | 8/1973 | Collins |
| 3,803,640 A | 4/1974 | Ericson |
| 3,858,243 A | 1/1975 | Pierron et al. |
| 3,881,474 A | 5/1975 | Krzewinski |
| 3,881,476 A | 5/1975 | Bolker et al. |
| 3,935,596 A | 2/1976 | Allen, Jr. et al. |
| 3,952,373 A | 4/1976 | Noorily |
| 3,956,048 A | 5/1976 | Nordgren |
| 3,968,792 A | 7/1976 | Small |
| 3,989,040 A | 11/1976 | Lofgren et al. |
| 4,000,521 A | 1/1977 | Zoephel et al. |
| 4,017,909 A | 4/1977 | Brandriff |
| 4,041,942 A | 8/1977 | Dougan et al. |
| 4,119,093 A | 10/1978 | Goodman |
| 4,134,398 A | 1/1979 | Scrivens |
| 4,153,054 A | 5/1979 | Boone |
| 4,214,320 A | 7/1980 | Belkin |
| RE30,520 E | 2/1981 | Pierron |
| 4,266,663 A | 5/1981 | Geraci |
| 4,290,148 A | 8/1981 | Roberts |
| 4,308,864 A | 1/1982 | Small et al. |
| 4,323,062 A | 4/1982 | Canty |
| 4,334,529 A | 5/1982 | Wirth |
| 4,384,573 A | 5/1983 | Elliott |
| 4,476,860 A | 10/1984 | Collins et al. |
| 4,479,492 A | 10/1984 | Singer |
| 4,489,720 A | 12/1984 | Morris et al. |
| 4,523,335 A | 6/1985 | Scrivens |
| 4,553,538 A | 11/1985 | Rafelson |
| 4,561,126 A | 12/1985 | Truman |
| 4,569,341 A | 2/1986 | Morris |
| 4,596,245 A | 6/1986 | Morris |
| 4,616,642 A | 10/1986 | Martin et al. |
| 4,627,427 A | 12/1986 | Arco |
| 4,631,756 A | 12/1986 | Scrivens |
| 4,664,103 A | 5/1987 | Martin et al. |
| 4,674,132 A | 6/1987 | Stein et al. |
| 4,705,171 A | 11/1987 | Eldridge |
| 4,711,236 A | 12/1987 | Glassman |
| 4,745,915 A | 5/1988 | Enright et al. |
| 4,783,854 A | 11/1988 | Bjorklund |
| 4,829,602 A | 5/1989 | Harreld et al. |
| 4,869,271 A | 9/1989 | Idris |
| 4,905,710 A | 3/1990 | Jones |
| 4,920,578 A | 5/1990 | Janzen et al. |
| 4,942,987 A | 7/1990 | Stackhouse |
| 4,951,318 A | 8/1990 | Harreld et al. |
| 5,010,592 A | 4/1991 | Skiles, Jr. |
| 5,029,344 A | 7/1991 | Shannon et al. |
| 5,033,115 A | 7/1991 | Bowling et al. |
| 5,042,507 A | 8/1991 | Dowdy |
| 5,061,246 A | 10/1991 | Anapliotis |
| 5,074,316 A | 12/1991 | Dowdy |
| 5,097,534 A | 3/1992 | Viemeister et al. |
| 5,109,873 A | 5/1992 | Marshall |
| 5,135,188 A | 8/1992 | Anderson et al. |
| 5,136,758 A | 8/1992 | Wilcox et al. |
| 5,140,996 A | 8/1992 | Sommers et al. |
| 5,345,946 A | 9/1994 | Butterworth et al. |
| 5,362,306 A | 11/1994 | McCarver et al. |
| 5,372,589 A | 12/1994 | Davis |
| 5,377,387 A | 1/1995 | Freed |
| D356,204 S | 3/1995 | Derrickson |
| 5,410,758 A | 5/1995 | Dupont et al. |
| 5,414,867 A | 5/1995 | Bowling et al. |
| 5,417,225 A | 5/1995 | Rubenstein et al. |
| 5,444,873 A | 8/1995 | Levin |
| 5,533,209 A | 7/1996 | Davis |
| 5,605,534 A | 2/1997 | Hutchison |
| 5,611,356 A | 3/1997 | Rothrum |
| 5,674,189 A | 10/1997 | McDowell et al. |
| 5,707,703 A | 1/1998 | Rothrum et al. |
| 5,765,566 A | 6/1998 | Rothrum |
| 5,778,889 A | 7/1998 | Jascomb |
| 5,778,891 A | 7/1998 | McMahan |
| 5,784,718 A | 7/1998 | Finnegan |
| 5,816,253 A | 10/1998 | Sosabee |
| 5,862,525 A | 1/1999 | Tankersley et al. |
| 5,867,825 A | 2/1999 | Scheerer |
| 5,916,202 A | 8/1999 | Ilaswell |
| 5,973,450 A | 10/1999 | Nishizawa et al. |
| 5,975,082 A | 11/1999 | Dowdy |
| 5,985,395 A | 11/1999 | Comstock et al. |
| 6,049,907 A | 4/2000 | Palomo |
| 6,062,444 A | 5/2000 | Tankersley et al. |
| 6,105,579 A | 8/2000 | Levitt et al. |
| 6,115,840 A | 9/2000 | Hastins |
| 6,138,278 A | 10/2000 | Taylor |
| 6,196,033 B1 | 3/2001 | Dowdle |
| 6,216,270 B1 | 4/2001 | Moquin et al. |
| 6,244,268 B1 | 6/2001 | Annett |
| 6,272,685 B1 | 8/2001 | Kumar |
| 6,285,611 B1 | 9/2001 | Kang |
| 6,345,622 B1 | 2/2002 | Chandler et al. |
| 6,405,730 B2 | 2/2002 | Levitt et al. |
| 6,378,136 B2 | 8/2002 | Matsushita |
| 6,536,636 B1 | 3/2003 | McDonniel |
| 6,564,386 B2 | 5/2003 | Fujikawa et al. |
| 6,694,981 B2 | 2/2004 | Gingles et al. |
| 6,742,522 B1 | 6/2004 | Baker et al. |
| 6,820,622 B1 | 11/2004 | Teves et al. |
| 6,843,252 B2 | 1/2005 | Harrison et al. |
| 7,114,500 B2 | 10/2006 | Bonutti |
| D533,982 S | 12/2006 | Graneto, III |
| 7,181,773 B1 | 2/2007 | Piraka |
| 7,237,271 B1 | 7/2007 | McLandrich |
| 7,290,547 B2 | 11/2007 | Joseph et al. |
| 7,293,654 B1 | 11/2007 | Wilson et al. |
| 7,305,991 B2 | 12/2007 | Santilli et al. |
| 7,412,728 B2 | 8/2008 | Alesina et al. |
| D579,178 S | 10/2008 | Snyder et al. |
| 7,454,798 B2 | 11/2008 | Feodoroff |
| 7,549,179 B1 | 6/2009 | Saied |
| D598,638 S | 8/2009 | Graneto, III |
| 7,654,266 B2 | 2/2010 | Corbitt, Jr. |
| 7,673,754 B2 | 3/2010 | Wilson, Jr. et al. |
| D622,479 S | 8/2010 | Herzog |
| D622,934 S | 9/2010 | Graneto, III |
| 7,841,020 B2 | 11/2010 | Mayfield et al. |
| 7,971,274 B2 | 7/2011 | Graneto, III |
| 8,006,836 B2 | 8/2011 | Trombetta |
| 8,069,495 B2 | 12/2011 | Kemper |
| 8,162,137 B2 | 4/2012 | Vellutato, Jr. et al. |
| 8,343,182 B2 | 1/2013 | Kirkham |
| 8,375,466 B2 | 2/2013 | Tasezen et al. |
| 8,464,374 B1 | 6/2013 | Thayer |
| 2002/0095709 A1 | 7/2002 | Fujikawa et al. |
| 2003/0060831 A1 | 3/2003 | Bonutti |
| 2003/0121522 A1* | 7/2003 | Gingles et al. ............... 128/853 |
| 2004/0019951 A1 | 2/2004 | Cioffi |
| 2004/0103904 A1 | 6/2004 | Auerbach et al. |
| 2005/0044608 A1 | 3/2005 | Ambrose et al. |
| 2005/0145254 A1 | 7/2005 | Aboul-Hosn et al. |
| 2005/0223468 A1 | 10/2005 | Hatton |
| 2005/0279366 A1 | 12/2005 | Adragna |
| 2006/0000002 A1 | 1/2006 | Bergkvist |

(56) References Cited

U.S. PATENT DOCUMENTS

| | | | |
|---|---|---|---|
| 2006/0081261 | A1 | 4/2006 | Corbin, Jr. |
| 2006/0117452 | A1 | 6/2006 | Ambrose |
| 2006/0117456 | A1 | 6/2006 | Griesbach |
| 2006/0191541 | A1 | 8/2006 | Aboul-Hosn et al. |
| 2006/0236440 | A1 | 10/2006 | Zahler |
| 2007/0102005 | A1 | 5/2007 | Bonutti |
| 2008/0006279 | A1 | 1/2008 | Bodenham |
| 2008/0023013 | A1 | 1/2008 | Tuke et al. |
| 2008/0047567 | A1 | 2/2008 | Bonutti |
| 2008/0178365 | A1 | 7/2008 | Furgerson et al. |
| 2009/0277460 | A1 | 11/2009 | Carrez et al. |
| 2009/0320177 | A1 | 12/2009 | Lin et al. |
| 2010/0031966 | A1* | 2/2010 | Allen .......................... 128/851 |
| 2010/0138975 | A1 | 6/2010 | Jordan et al. |
| 2010/0299805 | A1 | 12/2010 | Graneto, III |
| 2010/0300459 | A1 | 12/2010 | Lair |
| 2011/0024485 | A1 | 2/2011 | Porowski |
| 2011/0154554 | A1 | 6/2011 | Furlong |
| 2011/0167534 | A1 | 7/2011 | Wong et al. |
| 2011/0315150 | A1* | 12/2011 | Bream, Jr. .................... 128/855 |
| 2012/0060257 | A1 | 3/2012 | Herzog |
| 2012/0124722 | A1 | 5/2012 | Yadav et al. |
| 2012/0167896 | A1 | 7/2012 | Stang |
| 2012/0312308 | A1 | 12/2012 | Allen |
| 2013/0091616 | A1 | 4/2013 | Muche et al. |
| 2013/0276204 | A1 | 10/2013 | Pasko et al. |
| 2014/0007316 | A1 | 1/2014 | Tommarello et al. |
| 2014/0082816 | A1 | 3/2014 | Christopher |
| 2014/0173814 | A1 | 6/2014 | Yadav et al. |
| 2014/0215681 | A1 | 8/2014 | Goodman |
| 2015/0089712 | A1 | 4/2015 | Gamble |
| 2015/0096099 | A1 | 4/2015 | Vanneste |
| 2015/0113698 | A1 | 4/2015 | Gregerson-Brown |
| 2015/0208741 | A1 | 7/2015 | Pasko |

FOREIGN PATENT DOCUMENTS

| | | |
|---|---|---|
| EP | 0166124 | 1/1986 |
| FR | 2896146 | 7/2007 |
| JP | 2001-510704 | 8/2001 |
| WO | 8602258 | 4/1986 |
| WO | 99/04721 | 2/1999 |
| WO | 2001/030258 | 5/2001 |
| WO | 2007/083032 | 7/2007 |
| WO | WO-2011/038792 | 4/2011 |

OTHER PUBLICATIONS

Harris, Raymond E., "Non-Final Office Action", U.S. Appl. No. 12/537,961, filed Aug. 7, 2009; dated Nov. 9, 2011.
Vanatta, Amy B., "Notice of Allowance", U.S. Appl. No. 12/720,360, filed Mar. 9, 2012; dated Feb. 9, 2012.
Harris, Raymond E., "Final Office Action", U.S. Appl. No. 12/537,961, filed Aug. 7, 2009; dated Apr. 11, 2012.
Harris, Raymond E., "NonFinal OA", U.S. Appl. No. 12/537,961, filed Aug. 17, 2009; dated Jul. 17, 2012.
Lee, Cheol Soo "International Search Report", PCT/US2012/032122; Filed Apr. 4, 2012; dated Nov. 1, 2012.
Harris, Raymond E., "Final OA", U.S. Appl. No. 12/537,961, filed Aug. 7, 2009; dated Nov. 21, 2012.
Byun, Sung C., "PCT Search Report", PCT No. PCT/US2012/052079; Filed Aug. 23, 2012; dated Dec. 26, 2012.
Hicks, Victoria "NonFinal OA", U.S. Appl. No. 13/116,473, filed May 26, 2011; dated May 16, 2013.
Hicks, Victoria "Final OA", U.S. Appl. No. 13/116,473, filed May 26, 2011; dated Nov. 22, 2013,.
3M Product Clinical Data Summary for No. 1521, 3M Plastic Medical Tape, Jan. 1996 (2 pages).
3M Technical Information Sheet, Product No. 1521, Feb. 2007 (2 pages).
Description and Photographs of 75-1040 Fenestrated Snap Drape (as of Oct. 6, 2008) (1 page).
Description and Photographs of a Perforated Drape With Tear Line (as of Oct. 6, 2008) (1 page).
Description and Photographs of D-09875-001 Snap Drape (as of Oct. 6, 2008) (1 page).
Description and Photographs of Perforated Drapes (as of Oct. 6, 2008) (2 pages).
European Search Report for European Applicafion No. 09167307.9 dated Oct. 11, 2010 (5 pages).
Medical Single Coated Film Tapes Selection Guide—Polyolefin & Vinyl, Nov. 1996 (3 pages).
"Final OA", U.S. Appl. No. 14/086,798, filed Nov. 21, 2013; dated Feb. 1, 2016.
"First Office Action", CN Application No. 201280046346.4; Filed Sep. 11, 2012; dated Aug. 26, 2015.
"Medline Catalog", Full BodyDrapes by Halyard Health; Medline Catalog; http://www.medline.com/catalog/catalog.jsp; Unknown Publication date but believed to be prior to present application filing date.
"Medline Catalog", K-C100 Mayo Stand Covers by Halyard Health; Medline Catalog; http://www.medline.com/catalog/catalog.jsp; Unknown Publication date but believed to be prior to present application filing date.
"Medline Catalog", Midline Cath Picc Kits by Medikmark; Medline Catalog; http://www.medline.com/catalog/catalog.jsp; Unknown Publication date but believed to be prior to present application filing date.
"Medline Catalog", PICC Full Body Coverage Pack by Halyard Health; Medline Catalog; http://www.medline.com/catalog/catalog.jsp; Unknown Publication date but believed to be prior to present application filing date.
"Notice of Allowance", Japanese App No. 2015-531859; dated Nov. 24, 2016.
"Office Action", Australian Patent Application 2012304800; dated Nov. 22, 2016.
"Office Action", Canadian Office Action for Canadian Patent No. 2,674,951 dated May 4, 2011 (3 pages).
"Office ACtion", Chinese App No. 201280046346.4; dated Apr. 21, 2016.
"Office Action", Chinese App No. 201280046346.4; dated Oct. 21, 2016.
"Office Action", JP Application No. 2014-531859; dated May 2, 2016.
Chang, Bong Ho , "PCT Search Report and Written Opinion", PCT/US2012/054659; Filed Sep. 11, 2012; dated Feb. 26, 2013.
Gimenez Burgos, R , "Extended European Search Report", App No. 12834067.6-1659/2747697; Reference No. SJG/P131778EP00.
Gimenez Burgos, R , "Extended European Search Report", EP 12829356.0-1659/2747696; PCT/US2012052079; Reference No. SJG/P131402EP00; dated Feb. 16, 2015.
Haden, Sally C. , "Final OA", U.S. Appl. No. 13/276,232, filed Oct. 18, 2011; dated Jul. 17, 2013.
Haden, Sally C. , "NonFinal OA", U.S. Appl. No. 13/276,232, filed Oct. 18, 2011; dated Apr. 8, 2013.
Haden, Sally C. , "NonFinal OA", U.S. Appl. No. 13/925,617, filed Jun. 24, 2013; dated Aug. 14, 2013.
Haines, Kimberly , "Notice of Allowance", U.S. Appl. No. 13/116,473, filed May 26, 2011; dated May 2, 2017.
Hicks, Victoria , "Final OA", U.S. Appl. No. 13/589,640, filed Aug. 20, 2012; dated Jan. 2, 2015.
Hicks, Victoria , "NonFinal OA", U.S. Appl. No. 13/589,640, filed Aug. 20, 2012; dated Jun. 13, 2014.
Hicks, Victoria , "Notice of Allowance", U.S. Appl. No. 13/116,473, filed May 26, 2011; dated Aug. 15, 2017.
Pandika, Kylie , "Examination Report", Australian Patent Application No. 2012312845; Filed Sep. 23, 2011; dated Nov. 1, 2016.
Reed, Richard , "First Examination Report", Australian Application No. 2012259325; Exam Request dated Mar. 5, 2015; Reference No. 35210639/GCP; dated Nov. 30, 2015.
Wu, Jocelyn Mary , "NonFinal OA", U.S. Appl. No. 14/086,798, filed Nov. 21, 2013; dated Sep. 24, 2015.
"Extended European Search Report", EP Application No. 12790027.2; PCT/US2012/032122; dated Jan. 5, 2015.

(56) References Cited

OTHER PUBLICATIONS

Hicks, Victoria, "Notice of Allowance", U.S. Appl. No. 13/589,640, filed Aug. 20, 2012; dated Dec. 19, 2017.
Oprea, Karen, "NonFinal OA", Canadian Application No. 2,847,495; dated Jan. 22, 2018.
Sato, Tomoya, "NonFinal Office Action", Japanese Patent Application No. 2017-121386; dated Dec. 27, 2017.

* cited by examiner

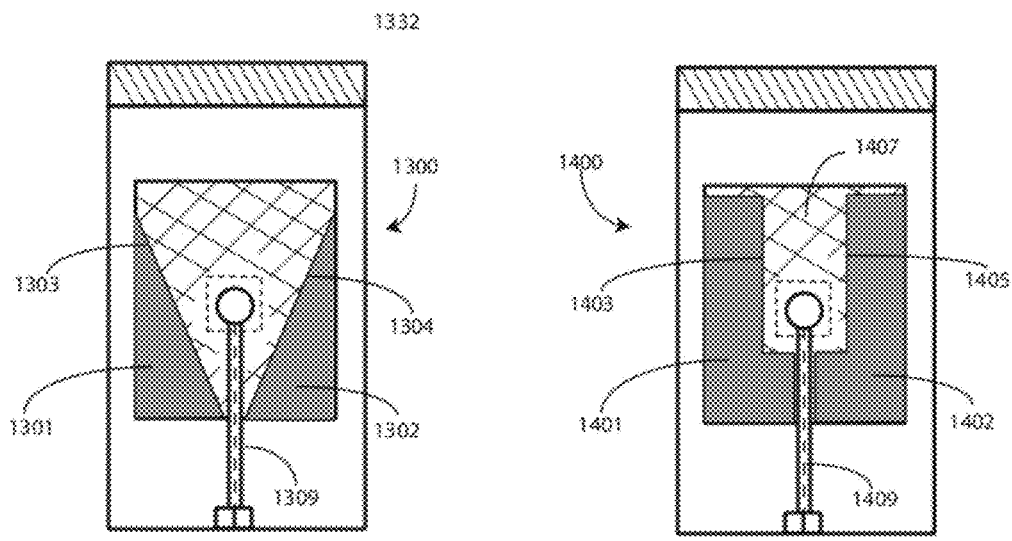
FIG. 13  FIG. 14
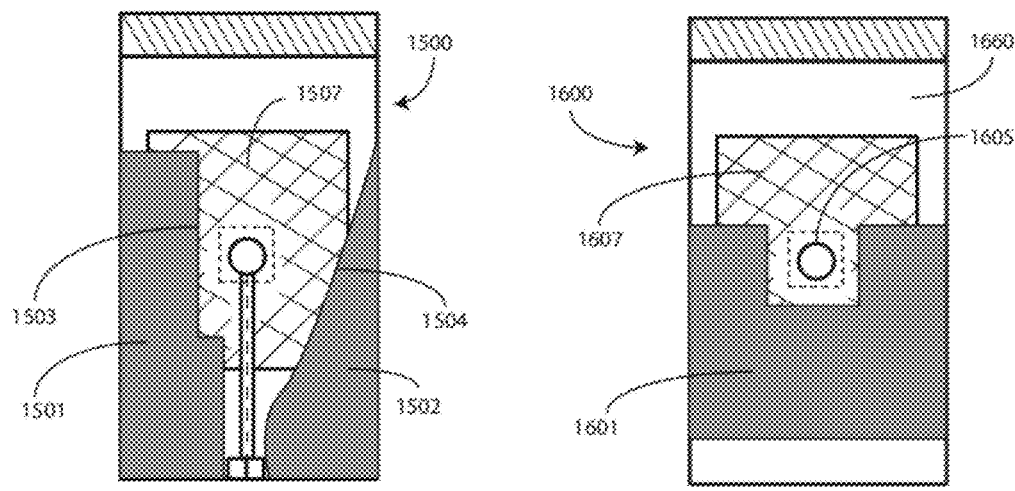
FIG. 15  FIG. 16

US 9,937,015 B2

SURGICAL DRAPE CONFIGURED FOR PERIPHERALLY INSERTED CENTRAL CATHETER PROCEDURES

CROSS REFERENCE TO PRIOR APPLICATIONS

This application is a continuation-in-part of U.S. application Ser. No. 13/116,473, filed May 26, 2011, which is incorporated herein by reference for all purposes.

BACKGROUND

Technical Field

This invention relates generally to medical drapes, and more particularly to a drape configured to facilitate prevention of infection and other complications during medical procedures.

Background Art

Healthcare facilities are increasingly concerned about the occurrence of secondary complications occurring during medical and surgical procedures. For example, during a medical procedure on an otherwise healthy patient, such as the insertion of an intravenous catheter, there is the possibility that a secondary infection or other complication can result. As a result, more attention is being turned to establishment and maintenance of sterile fields about patients and procedure sites during medical procedures. For example, some healthcare facilities request medical professionals to check and double check certain conditions, such as whether a proper sterile field has been established or whether a proper sterile field can be maintained. Despite these warnings, it can some times be difficult to remember to check and double check each condition. Further, it can be difficult to maintain sterile fields with some currently existing equipment.

It would be advantageous to have equipment configured to reduce contamination of sterile fields during medical procedures.

BRIEF DESCRIPTION OF THE DRAWINGS

FIGS. 9-16 illustrate various radial drape attachments having fluid collection pouches configured in accordance with one or more embodiments of the invention.

Figure 1:
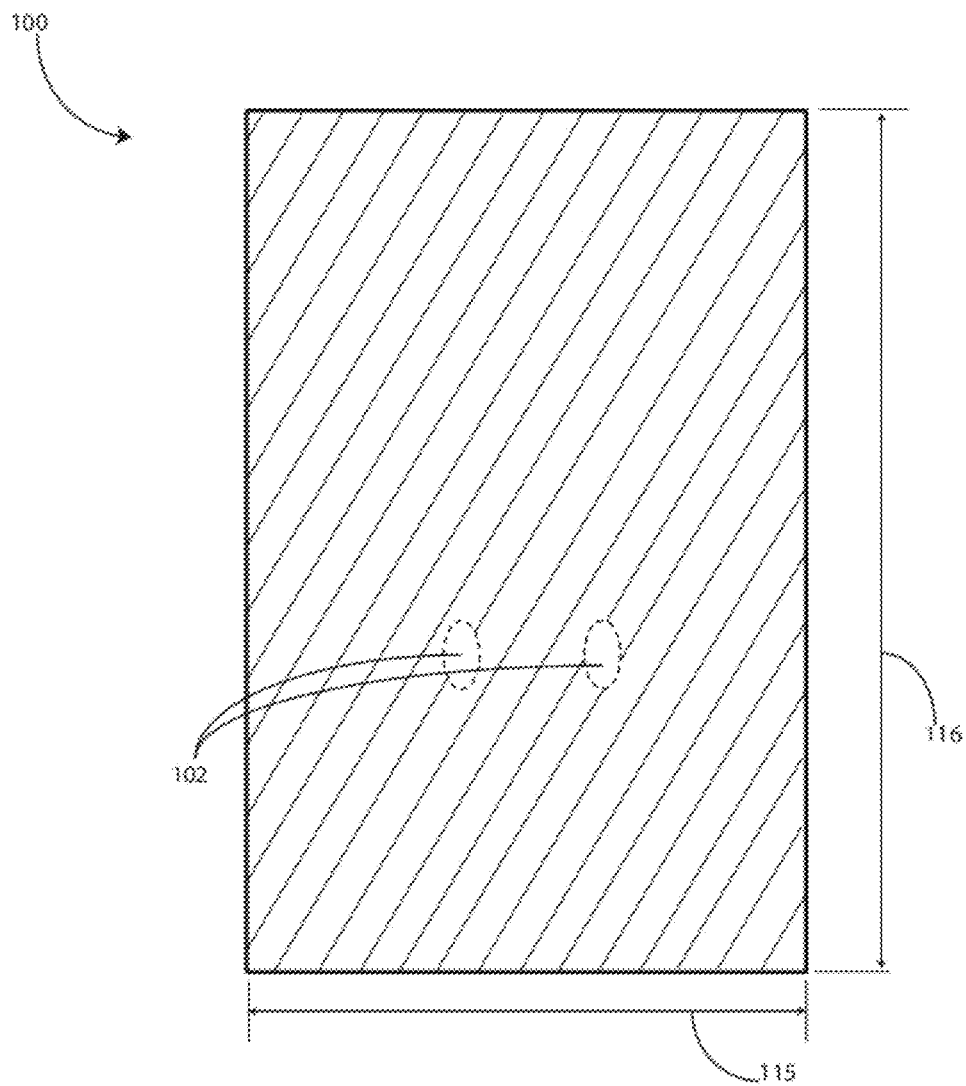
FIG. 1 illustrates one embodiment of a patient drape configured in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

A central catheter is a catheter that is placed into a large vein through which medical professionals may deliver fluids, dyes, or medications to a patient. For example, during angiogram procedures, medical professionals will insert a central catheter into an artery or vein. The catheter is then directed to the proper area within the patient. A special dye is then injected into the vessel so that the circulatory system will be visible to a radiographic camera.

Central catheters can also be used to withdraw fluids, such as blood, for testing. Central catheters can be inserted into various parts of the patient. During angiograms, catheters can be inserted into a blood vessel near the groin, such as the femoral artery or vein, but can also be placed into vessels in the arm. Placement into vessels in the arm can be advantageous in angiogram procedures that study the circulatory system about the heart, because the path through which the catheter must be guided is shorter from the arm to the heart than from the groin to the heart. Central catheters inserted into arms are generally known as "peripherally" inserted central catheters. Peripherally inserted central catheters can be placed into a patient's arm for diagnostic procedures, such as angiograms. Peripherally inserted central catheters can also be placed in a patient's arm to allow prolonged intravenous access, such as for extended antibiotic treatment, chemotherapy, and so forth. In the former case, insertion is temporary. In the latter, peripherally inserted central catheters can be left in place in the patient's arm for periods ranging from six weeks to one year.

Catheter insertion procedures, including peripherally inserted central catheter procedures, are generally performed bedside or in a diagnostic lab room by a medical professional who specializes in catheter insertion. The medical professional is frequently a specially trained nurse. One exception to bedside insertion occurs during radiology procedures, such as angiograms, where the catheter is guided and inserted by a doctor.

Regardless of who inserts the catheter, or where it is inserted, bloodstream infection is continually a concern. It will be readily understood that insertion of a foreign object, which can be on a semi-permanent basis, into a patient's vein has associated therewith a risk that bacteria or other microbes will be introduced into the bloodstream during central catheter and peripherally inserted central catheter insertion procedures. Studies have shown that such infections can be a source of death. The largest percentage of these infections occurs at the time of catheter insertion.

To combat this, some health care providers have begun to issue catheter insertion procedure requirements that are similar to those used in surgery. For example, a catheter insertion specialist must don hair covering, a mask, gloves, foot coverings, and a full-body sterile surgical gown, just as if they were entering an operating room. Such procedures also require the patient to be covered by a conventional medical drape. Such procedures attempt to ensure that a maximum barrier environment is established prior to the insertion of central lines.

While the procedures are beneficial, they are insufficient for preventing bloodstream infections during central line procedures for two reasons: First, it is frequently the case that medical personnel performing line placement are unfamiliar with "surgical" practices and aseptic techniques used during operations. Said differently, central catheter insertion personnel generally do not work in the operating room, and are therefore frequently unacquainted with operating room procedures. Accordingly, such personnel therefore frequently lack understanding of certain techniques, including correct steps in tying tourniquets and when to drape the patient. These deficiencies can cause breaks in aseptic technique. For example, tying a tourniquet too soon could cause damage to the patient. Nonetheless, in catheter insertion, procedures frequently suggest the tourniquet be tied before the sterile field is created, which is still before the medical personnel dons the equipment listed above. Thus, some medical personnel may be tempted to apply tourniquets required in central line insertion procedures too soon.

A second problem is that a single person—rather than a team—generally inserts central catheters and peripherally inserted central catheters. Consequently, the insertion specialist must juggle many items and perform many complex steps to ensure sterile fields using conventional equipment and drapes. Application of prior art drapes requires at least two people to prevent compromising the sterile field. When one person attempts to apply a drape in a catheter insertion procedure, he or she risks compromise of any sterile field that may be required for the procedure.

Embodiments of the present invention work to solve both problems by providing a full body procedural drape that is specifically configured for central catheter insertions. While peripherally inserted central catheters will be used below as an illustrative application, it will be clear to those of ordinary skill in the art having the benefit of this disclosure that the invention is not so limited. Minor modification of drapes described herein, such as slight movement and relocation of the components described below, will permit drapes configured in accordance with embodiments of the invention to be readily used for a wide variety of central line or catheterization procedures.

Embodiments of the invention described herein are configured in a modular arrangement, with a medical drape including a patient drape and a radial drape attachment. The patient drape is opaque in one embodiment, and is configured for placement over the patient. The radial drape attachment is equipped with an adhesive or other coupling that allows it to be attached to the patient drape. The radial drape attachment can be attached to the patient drape such that it extends beyond a perimeter of the patient drape in any radial alignment relative to the patient drape. In one or more embodiments, the radial drape attachment is coupled to the patient drape such that it covers a patient's arm sticking out from beneath the patient drape. The combined patient drape/radial drape attachment thus allows catheter insertion while completely maintaining a sterile field on a patient side of the medical drape.

Advantages offered by the embodiments of the invention, as compared to prior art designs, include helping medical personnel more easily apply, use, and remove the drape. Additionally, some embodiments assist in the application of tourniquets used during catheter insertion procedures. The drape assemblies described below help to ensure proper aseptic techniques. They also help in drape removal without compromising the integrity of the catheter that has been inserted into the patient. A predominant additional advantage offered by embodiments of the invention is that the drapes described below can be applied by a single person without compromising the sterile field about the patient.

Embodiments described below provide a medical drape, suitable for use in peripherally inserted central catheter and other procedures, that work as full-body drapes, and that are easy for one person to open and apply. Additionally, medical drapes described below can be universally configured for use with the right or left arm of a patient. In contrast to conventional drapes, which are fully opaque, embodiments described below include radial drape attachments that have transparent portions. The transparent portions make it possible for medical personnel to see the patient's arm through the radial drape attachment for better application and removal of tourniquets and for better insertion of catheters.

Some embodiments include tourniquets that are integrated in the radial drape attachments. Where included, the integral tourniquet prevents medical personnel from "fishing" for a tourniquet that is beneath an opaque drape, as is the case in prior art designs. The tourniquets can include closure devices on the patient side of the drape, such as snap-locking devices or buckle-type closures.

In one or more embodiments, the radial drape attachment of the medical drape includes a tool-less removal feature that allows drape components to be easily removed at the end of the procedure. The tool-less removal feature allows the radial drape attachment to "break away" from the insertion site, thereby preventing accidental tugging or pulling of the remaining catheter line.

Figure 2:
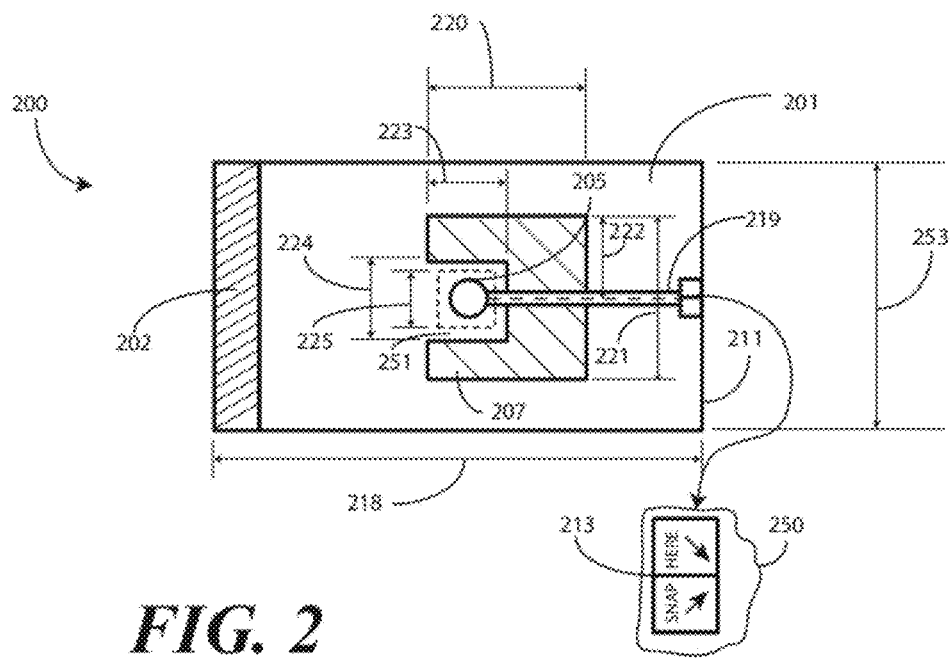
FIG. 2 illustrates a non-patient side of one radial drape attachment configured in accordance with one or more embodiments of the invention.
Figure 3:
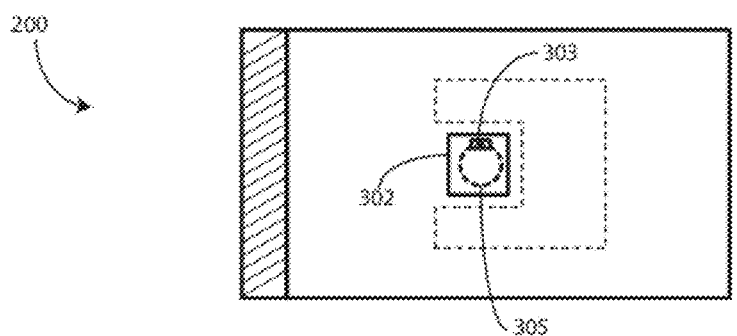
FIG. 3 illustrates a patient side of one radial drape attachment configured in accordance with one or more embodiments of the invention.

Turning now to FIGS. 1-3, illustrated therein is one embodiment of a medical drape configured in accordance with one or more embodiments of the invention, and suitable for peripherally inserted central catheter and other catheterization procedures. FIG. 1 illustrates a plan view of patient drape 100, while FIGS. 2 and 3 illustrate plan views of a radial drape attachment 200. FIGS. 1 and 2 illustrates the "non-patient" or "medical personnel" side of the patient drape 100 and radial drape attachment 200, respectively, while FIG. 3 illustrates a plan view of the "patient side" of the radial drape attachment 200. The side of FIG. 3 is referred to as the "patient side" because it is the side that will contact the patient when the medical drape is used in a catheter insertion procedure. The medical drape is modular in that it comprises multiple components, i.e., the patient drape 100 and the radial drape attachment 200.

Beginning with FIG. 1, the patient drape 100 is configured to at least over the torso portions of the patient. Generally, these torso portions will be at least inferior to the neck portion of the patient. In one or more embodiments, the patient drape 100 is opaque. For example, the patient drape 100 can be manufactured from 45g spunbond-meltblown-spunbond material. Other materials can be used for the patient drape 100, including, for example, various woven, non-woven, hydroentangled materials, and/or combinations thereof, absorbent Airlaid, spunlace, blends of polyester, polypropylene, polyethylene, urethane, and/or combinations thereof, using various methods, including a spunbond metblown spundbond (SMS) method, a spunbond metblown metblown spundbond method (SMMS), and a spunbond metblown metblown spundbond method (SMMMS). Suppliers of such materials include Cardinal Health in Dublin, Ohio, Kimberly Clark in Neena, Wis., Molnycke Health Care in Newtown, Pa., and Precept Medical Products, Inc., in Arden, N.C. These materials and methods are illustrative only, as others will be readily apparent to those of ordinary skill in the art having the benefit of this disclosure. For example, one or more antimicrobial layers can be added to further enhance antimicrobial protection. Additionally, the material can optionally include and water resistant lining that prevents the passage of fluids through the material.

In one or more embodiments, the patient drape 100 has a length 116 of between 95 and 110 inches, such as about 104 inches plus or minus an inch. In one embodiment, the patient drape has a width 115 of sixty-four inches, plus or minus one inch. The term "about" is used to refer to a measurement inclusive of manufacturing tolerances. Accordingly, both 104.5 and 103.1 inches would be "about" 104 inches if the manufacturing tolerances were plus or minus one inch.

In certain applications, the patient drape 100 can be configured with optional incise features 102 designed for a particular medical procedure. The incise features 102 may be apertures. In other embodiments, the incise features 102 may be fenestrations that can be opened to form apertures in the patient drape 100. For example, where the patient drape 100 is used in angioplasty procedures, a pair of incise features 102 may be disposed in a location so as to be located above a patient's groin when the patient drape 100 is placed atop a patient. This location would provide access to the patient's femoral artery or vein during the angioplasty procedure. It will be clear to those of ordinary skill in the art having the benefit of this disclosure that the inclusion of incise features 102 is optional. Further, where included, the number and location of incise features 102 can vary based upon application.

FIGS. 2 and 3 illustrate the radial drape attachment 200. The radial drape attachment 200, in one embodiment, includes a radial drape attachment layer 201 and an adhesive coupling 202. In the illustrative embodiment of FIGS. 2 and 3, the radial drape attachment layer 201 is transparent, and forms a transparent portion of the radial drape attachment 200. For example, the radial drape attachment layer 201 can be manufactured from 0.065 millimeter clear polyethylene. The radial drape attachment layer 201 can also be translucent or pellucid. For example, in a transparent embodiment the radial drape attachment layer 201 can be manufactured from clear 0.05 mm polyethylene sheeting. It should be noted that other clear, flexible materials may be used in place of polyethylene. The adhesive coupling 202 is attached to the transparent portion in this illustrative embodiment.

In one embodiment, the adhesive coupling 202 is a layer of adhesive tape with a width of two inches. The adhesive portion of the adhesive tape is disposed on the patient side of the radial drape attachment layer 201. The adhesive portion can be covered with a releasable covering. When the radial drape attachment 200 is ready for use, the releasable covering can be removed to reveal the adhesive material. Pressing the adhesive material against the patient drape 100 causes the radial drape attachment 200 to be coupled to the patient drape 100. It will be clear to those of ordinary skill in the art having the benefit of this disclosure that other coupling devices can be used for the adhesive coupling 202. Examples include hook and loop fasteners, mechanical clasps, or other fasteners. The adhesive coupling 202 need only be configured to attach the radial drape attachment 200 to the patient drape 100.

Figure 4:
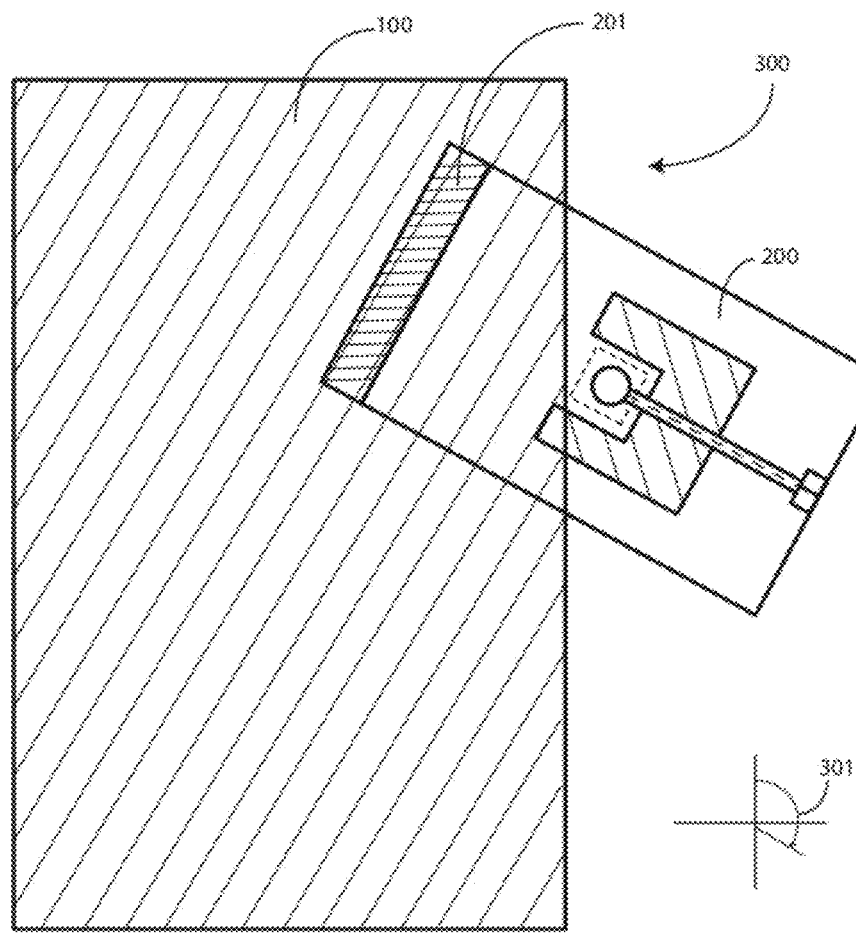
FIG. 4 illustrates one medical drape having a patient drape and a radial drape attachment configured in accordance with one or more embodiments of the invention.

Turning briefly to FIG. 4, illustrated therein is the medical drape 300 formed when the adhesive coupling 202 of the radial drape attachment 200 has been coupled to the patient drape 100. The adhesive coupling 202 adheres the radial drape attachment 200 to the patient drape 100 during a catheter insertion procedure. It should be noted that the modular nature of the medical drape 300 allows the radial drape attachment 200 to be adhered to the patient drape 100 in any radial alignment. Said differently, a medical services provider can attach the adhesive coupling 202 at any point along the patient drape 100, and at any and at any radial alignment 301 relative to the patient drape 100. This makes the medical drape 300 fully customizable. Further, the geometric configuration of the medical drape 300 can be selected based upon the patient's body shape, position during the procedure, or procedure being performed. Where the adhesive coupling 202 comprises a releasable adhesive, the radial drape attachment 200 can be repositioned as necessary as well. This modular arrangement offers a distinct advantage over prior art drapes in that the overall configuration of the medical drape 300 can vary from patient to patient and procedure to procedure.

Turning back to FIGS. 2 and 3, it should be noted that configuring the radial drape attachment layer 201 to be pellucid, translucent, or transparent offers several additional advantages over prior art drapes. First, it allows the insertion specialist to see the insertion site during the insertion procedure. Second, it allows the insertion specialist to monitor the limb into which the catheter is inserted. The insertion specialist can watch, for example, for color changes in the limb that may be indicative of a procedural complication. Third, when tourniquets are used, as is frequently the case with peripherally inserted central catheters, the pellucid or transparent nature of the radial drape attachment layer 201 allows the insertion personnel to quickly find and use the tourniquet.

In one or more embodiments, the radial drape attachment 200 includes one or more apertures configured for a medical procedure. For example, the illustrative radial drape attachment 200 of FIGS. 2 and 3 includes an fenestration 205 configured for placement over a central catheter insertion site. The fenestration 205 can be configured as a fenestration in the radial drape attachment 200 that defines an opening or potential aperture in one or more embodiments. The fenestration 205, in one embodiment, is configured to allow a peripherally inserted central catheter to be inserted through the fenestration 205 when the radial drape attachment 200 is coupled to the patient drape 100 to form a medical drape 300 disposed atop the patient. The fenestration 205 or fenestrations could be configured to accommodate other medical procedures as well.

In one or more embodiments, a support layer is disposed about the fenestration 205. In the illustrative embodiment of FIGS. 2 and 3, the support element comprises an absorptive element 207 manufactured from absorptive material and disposed about the fenestration 205. In this illustrative embodiment, the absorptive element 207 has a substantially U-shaped area and is placed about the fenestration 205 on a side that is opposite the adhesive coupling 202. The absorptive element 207 can be a gauze-like, a non-woven absorbent material, or other absorptive material configured to absorb fluids, such as blood, that may become present during a catheterization procedure.

In one embodiment, the absorptive element 207 is arranged such that a predetermined minimum area 251 of the radial drape attachment layer 201 is disposed between the absorptive element 207 and the fenestration 205. In this illustrative embodiment, the predetermined minimum area 251 is a one and a half inch wide strip that passes about the fenestration 205 on three sides. The predetermined minimum area 251 of the radial drape attachment layer 201, which in this example is transparent, can be helpful in a variety of applications. For example, in angioplasty applications, an ultrasound technician may need to see the patient's limb through the radial drape attachment 200. If the absorptive element 207 extends to the fenestration 205, this is not possible. However, when the predetermined minimum area 251 is included, the patient's limb disposed beneath the radial drape attachment 200 becomes visible from above.

In one or more embodiments, to keep the fenestration 205 closed until needed, a releasable covering 302 may be attached over the fenestration 205. In this illustrative embodiment, the releasable covering 302 comprises a conventional medical release paper that is affixed across the fenestration 205 to the patient side of the radial drape attachment 200. One suitable means for affixing the releasable covering 302 to the radial drape attachment 200 is with a section 303 of adhesive tape. The adhesive tape can be a single-coated polyethylene medical tape, such as a medical tape manufactured by 3M (St. Paul, Minn.) as product number 1521. The 3M Medical Tape 1521 is a single-coated tape having a matte finish which includes a transparent polyethylene and is coated with a hypoallergenic, pressure sensitive acrylate adhesive and includes a liner that is silicone treated and is polyethylene coated on one side only along with a bleached Kraft paper release liner. The 3M medical tape has a tape caliper of 6.4 mil (0.16 mm) of polyethylene film tape, a backing of 5.0 mil (0.13 mm) translucent polyethylene film, an acrylate adhesive (designed for medical/surgical use), and a release liner of 83 lb poly-coated Kraft paper, with silicone on one side (6 mils/0.15 mm). The adhesion to steel of the 3M Medical Tape 1521 is 21 ounces/inch width (0.6 kg/25 mm width). Other suitable medical tapes manufactured by 3M and/or other manufacturers may be used as well. For example, where the adhesive tape is double-sided, the tape can also be used to temporarily attach the radial drape attachment 200 to the patient. This ensures that the fenestration 205 remains over the insertion site without requiring the insertion specialist to continually hold the radial drape attachment 200 in place.

In one or more embodiments, to make removal of the radial drape attachment 200 easier, a tool-less removal feature 209 can be incorporated into the radial drape attachment 200. One example of a tool-less removal feature is described in commonly assigned, co-pending patent application U.S. Ser. No. 12/188,931, filed Aug. 8, 2008, entitled "Zip Strip Draping System and Methods of Manufacturing Same," Fred L. Allen, inventor, which is incorporated herein by reference.

In one embodiment, the tool-less removal feature 209, which is described in more detail with reference to FIG. 17 below, includes a drape cut, adhesive tape strip, and score line, each of which extends from an edge 211 of the radial drape attachment 200 to the fenestration 205. In the illustrative embodiment of FIGS. 2 and 3, the tool-less removal feature 209 extends from an edge 211 of the radial drape attachment 200, across the absorptive element 207, and across the predetermined minimum area 251 of the radial drape attachment layer 201 to the fenestration 205. Said differently, the drape cut, adhesive tape strip, and score line can begin at an edge, e.g., edge 211, and pass along the radial drape attachment layer 201 to an aperture, e.g., fenestration 205.

The adhesive tape strip is positioned along the length of the drape cut to overlap a portion of the radial drape attachment layer 201 on both sides of the drape cut to initially secure the adjoining drape cut sides together. The score line permits easy tearing of the adhesive tape strip to open the drape cut. Usage of the tool-less removal feature 209 allows the radial drape attachment 200 to be removed around a catheter that has been placed through the fenestration 205 without disturbing the catheter.

In one or more embodiments, to show medical personnel where to begin opening the tool-less removal feature 209, an indicator 213, shown in a blown-up view 250 in FIG. 2, can be disposed at the edge 211 of the radial drape attachment 200. Said differently, the indicator 213 can be included to indicate the starting point of the tool-less removal feature 209. The indicator 213 may include instructional indicia such as the words "Tear Here" or "Snap Here." The indicator 213 instructs a person to grasp and pull apart the indicator elements to tear apart the adhesive tape strip along the score line. This allows the person to "peel" the radial drape attachment layer 201 about the inserted catheter or central line.

Illustrative dimensions now are provided to further describe one embodiment suitable for use in peripherally inserted central catheter applications. It will be clear to those of ordinary skill in the art having the benefit of this disclosure that these dimensions are examples only, provided to present a clearer image of one embodiment, and can readily be modified based upon application or customer demand.

In one embodiment, the radial drape attachment 200 has a length 118 of forty-eight inches, plus or minus one inch. In one embodiment, the radial drape attachment 200 has a width 253 of forty-six inches, plus or minus one inch.

In the illustrative embodiment of FIGS. 2 and 3, the width 220 of the absorptive element 207 is about twenty inches. The length 221 of the absorptive element 207 is about twenty inches. The absorptive element 207 extends a distance 222 of about ten inches from the center of the fenestration 205. The "arms" of the U-shape of the absorptive element 207 has a width 223 of about ten inches. The center of the U-shape of the absorptive element 207 is a distance 224 of about ten inches. The width 225 of the releasable covering 302 is about seven inches. These illustrative dimensions are not intended to be limiting, but are instead included to provide an example of one set of dimensions suitable for catheter insertion procedures.

Figure 5:
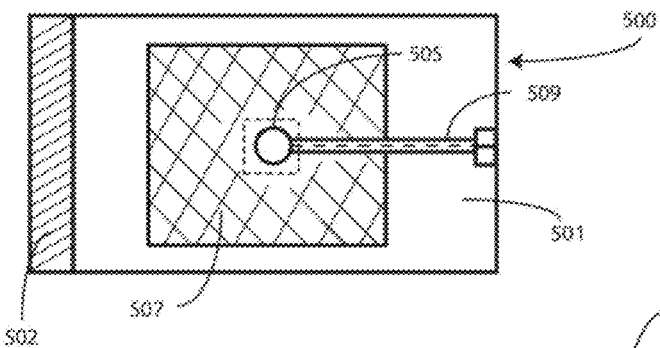
FIGS. 5-8 illustrate alternate radial drape attachments configured in accordance with one or more embodiments of the invention.

Turning now to FIG. 5, illustrated therein is an alternate radial drape attachment 500 suitable for attachment to a patient drape (100) to form a medical drape in accordance with embodiments of the invention. As with the radial drape attachment (200) of FIGS. 2 and 3, the radial drape attachment 500 includes a radial drape attachment layer 501 and an adhesive coupling 502. The radial drape attachment layer 501 of FIG. 5 is pellucid. The adhesive coupling 502 is attached to the pellucid portion of the radial drape attachment layer 501 in this illustrative embodiment. Pressing the exposed adhesive coupling 502 against a patient drape (100) couples the radial drape attachment 500 to the patient drape (100) to form a medical drape.

Also as with FIGS. 2 and 3, the radial drape attachment 500 of FIG. 5 includes an aperture 505 configured for a medical procedure, such as for placement over a central catheter insertion site. To make removal of the radial drape attachment 500 from the patient easier, a tool-less removal feature 509 is incorporated into the radial drape attachment 500.

The radial drape attachment 500 of FIG. 5 differs from previous embodiments by way of the support layer 507. In the embodiment of FIG. 5, the support layer 507 comprises a fluid impervious material. An absorptive layer can also be integrated into the support layer 507 as well. The support layer 507 is disposed completely about the aperture 505, rather than having a U-shape as described above. The support layer 507 provides a reinforcing structure for the radial drape attachment layer 501, and helps to ensure that fluids or other materials do not pass through the radial drape attachment 500.

Figure 6:
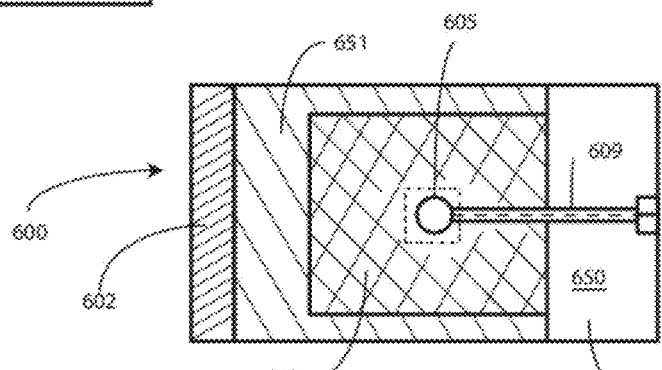

Turning to FIG. 6, illustrated therein is another radial drape attachment 600. In this illustrative embodiment, the radial drape attachment layer 601 is bifurcated into two sections. A first section 650 is transparent, while a second section 652 is opaque. For example, the first section 650 can be manufactured from clear polyethylene, while the second section 651 is manufactured from an opaque material, such as spunbond-meltblown-spunbond material. While an opaque second section 651 prevents the insertion specialist for seeing a patient's limb except through the fenestration 605, the transparent first section 650 allows the insertion specialist to see the circulation in the fingers of the patient without manipulating the radial drape attachment 600.

The second section 651 is disposed between the first section 650 and the adhesive coupling 602. This results in the adhesive coupling 602 being coupled to the opaque portion of the radial drape attachment 600 and the fenestration 605 being disposed along the opaque portion of the radial drape attachment layer 601, rather than along the transparent portion as was the case in FIG. 5. This radial drape attachment 600 includes a tool-less removal feature 509 as well. The support layer 607 of this embodiment is a combined absorptive/fluid impervious material having absorptive properties on the non-patient side and a fluid impenetrable backing underneath.

Figure 7:
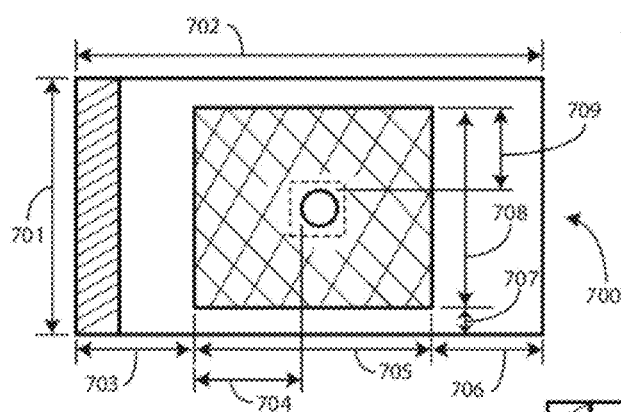
Figure 8:
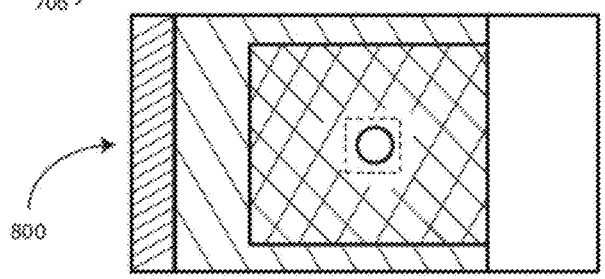

Not all radial drape attachments need to include the tool-less removal feature. Turning to FIG. 7, illustrated therein is a radial drape attachment 700 that is similar to that shown in FIG. 5, but without the tool-less removal feature. FIG. 8 illustrates a radial drape attachment 800 similar to that shown in FIG. 6, but without the tool-less removal feature.

FIG. 7 provides some illustrative dimensions for one explanatory embodiment. It should be understood that these dimensions can be varied without departing from the spirit and scope of the disclosure. The length 702, in one embodiment is forty-eight inches plus or minus one inch. The width 701 is forty-six inches plus or minus one inch. The adhesive coupling can be configured as one strip of double-sided tape that is two inches wide.

Length 703 is ten inches in one embodiment, while length 704 is twelve inches. Length 705 is twenty inches in one embodiment, while length 706 is eighteen inches. Length 707 is thirteen inches in one embodiment, while length 708 is twenty inches. Length 709 can be eight inches. Other dimensions, suitable for other applications, will be obvious to those of ordinary skill in the art having the benefit of this disclosure.

In one or more embodiments, pouches can be integrated along the radial drape attachment. In one embodiment, the pouches can be useful for temporarily storing small tools or medical implements during a medical procedure. In other embodiments, the pouches can be configured to catch fluids passing along a surface of the radial drape attachment. Catching fluids can be advantageous in that it prevents them from flowing to the floor, which can cause slippery conditions or increased probability of someone falling.

Turning now to FIGS. 9-12, illustrated therein are radial drape attachments 900,1000,1100,1200 having pouches 901, 902,1001,1002,1101,1102,1201,1202 disposed along the radial drape attachments 900,1000,1100,1200 about the fenestrations 905,1005,1105,1205. These pouches 901,902, 1001,1002,1101,1102,1201,1202 are disposed atop the support layers 907,1007,1107,1207 of each radial drape attachment 900,1000,1100,1200. Each of the pouches 901, 902,1001,1002,1101,1102,1201,1202 includes an side 903, 904,1003,1004,1103,1104,1203,1204 facing the fenestration 905,1005,1105,1205 that is open. The remaining sides of each pouch 901,902,1001,1002,1101,1102,1201,1202 are attached to the radial drape attachment 900,1000,1100,1200, thereby being closed.

Figure 9:
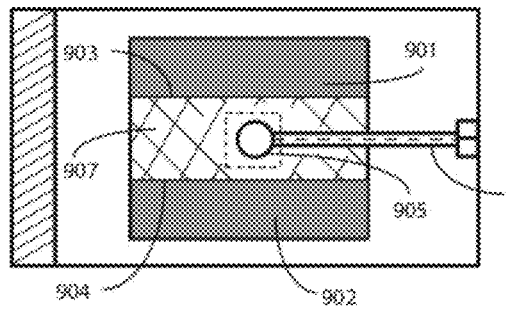
Figure 10:
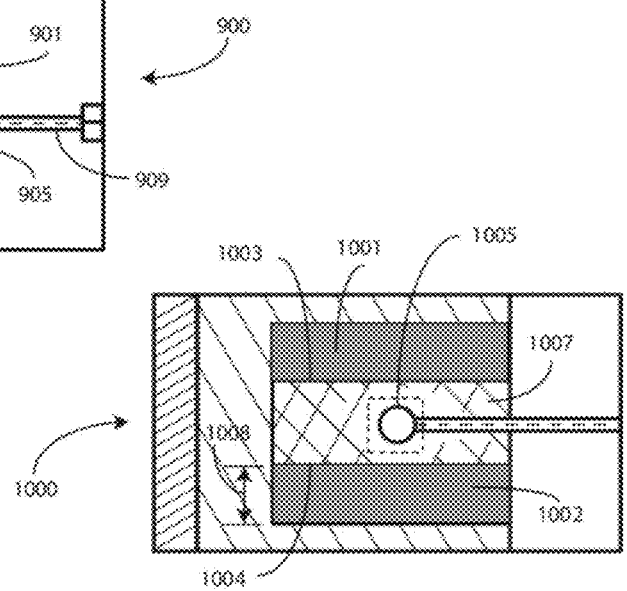

The radial drape attachment 900 of FIG. 9 is similar to that shown in FIG. 6. However, two pouches 901,902 have been disposed on either side of the tool-less removal feature 909. A first pouch 901 is disposed on a first side of the tool-less removal feature 909, while a second pouch 902 is disposed on a second side of the tool-less removal feature 909. The radial drape attachment 1000 of FIG. 10 is similar to that shown in FIG. 7. However, two pouches 1001,1002 have been disposed on either side of the tool-less removal feature 1009. A first pouch 1001 is disposed on a first side of the tool-less removal feature 1009, while a second pouch 1002 is disposed on a second side of the tool-less removal feature 1009. In one embodiment, the first pouch 1001 and second pouch 1002 have a width of about five inches, and can be separated from the support layer 1007 by a distance of one inch. As noted in the discussion of FIG. 7, the first pouch 1001 and second pouch 1002 can be about twenty inches in length.

Figure 11:
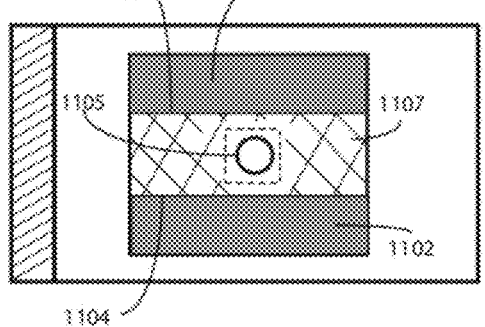
Figure 12:
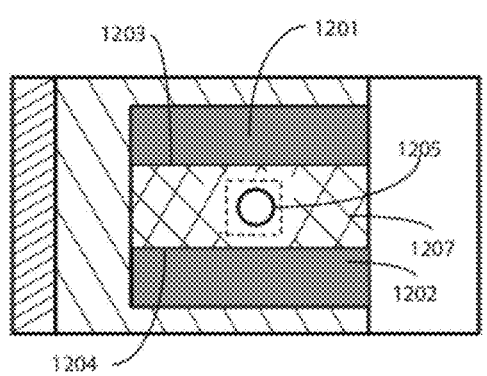

The radial drape attachments 1100,1200 of FIGS. 11 and 12 are similar to those shown in FIGS. 7 and 8, respectively. However, pouches 1101,1102,1201,1202 have been disposed on opposite sides of the fenestrations 1105,1205.

Note that the pouches shown in FIGS. 9-12 are illustrative in shape and placement only. It will be clear to those of ordinary skill in the art having the benefit of this disclosure that other shapes and placements are also possible. For example, turning to FIG. 13, illustrated therein is a radial drape attachment 1300 where the pouches 1301,1302 are triangular in shape. Presuming that the adhesive coupling 1332 is coupled to a patient drape (100) along a patients chest when the patient is lying on their back, and presuming the radial drape attachment 1300 is covering an arm that is extended away and downward from the patient, the triangular configuration of the pouches 1301,1302 will tend to "catch" more fluid than will the pouches (901,902,1001, 1002,1101,1102,1201,1202) of FIGS. 9-12. In the illustrative embodiment of FIG. 13, a first pouch 1301 is disposed on a first side of the tool-less removal feature 1309, while a second pouch 1302 is disposed on a second side of the tool-less removal feature 1309. The "triangles" of FIG. 13 are illustratively shown as right triangles, and are turned such that their hypotenuses 1303,1304 facing the fenestration 1305 and forming openings. The remaining sides of each pouch 1301,1302 are closed.

Turning to FIG. 14, illustrated therein is a radial drape attachment 1400 where the pouches 1401,1402 have an "L" shape. A first pouch 1401 is disposed on a first side of the tool-less removal feature 1409, while a second pouch 1402 is disposed on a second side of the tool-less removal feature 1409. The "L-shapes" of FIG. 14 are turned such each "L" faces the fenestration 1405. The interior L-shapes 1403,1404 form openings, with the remaining sides of each pouch 1401,1402 being closed.

Turning to FIG. 15, illustrated therein are alternate pouch shapes. Pouch 1501 is an L-shape that passes not only across the support layer 1507, but also the transparent region 1500 as well. The interior L-shape 1503 faces the fenestration 1505 and forms an opening, with the remaining sides of the pouch 1502 being closed. Pouch 1502 is configured as a curvilinear polygon with a curved opening 1504 facing the fenestration 1505.

Turning to FIG. 16, illustrated therein is another pouch shape. The pouch 1601 is U-shaped and passes along three sides of the fenestration 1605, as no tool-less removal feature is included in this radial drape attachment 1600. As with FIG. 15, the pouch 1601 passes along both the support layer 1607 and the transparent layer 1660. It will be clear to those of ordinary skill in the art having the benefit of this disclosure that any number of pouch shapes, sizes, and placements can be used with radial drape attachments of the present invention. For example, curvilinear pouches and triangular pouches can be used in combination in different locations, and so forth.

Figure 17:
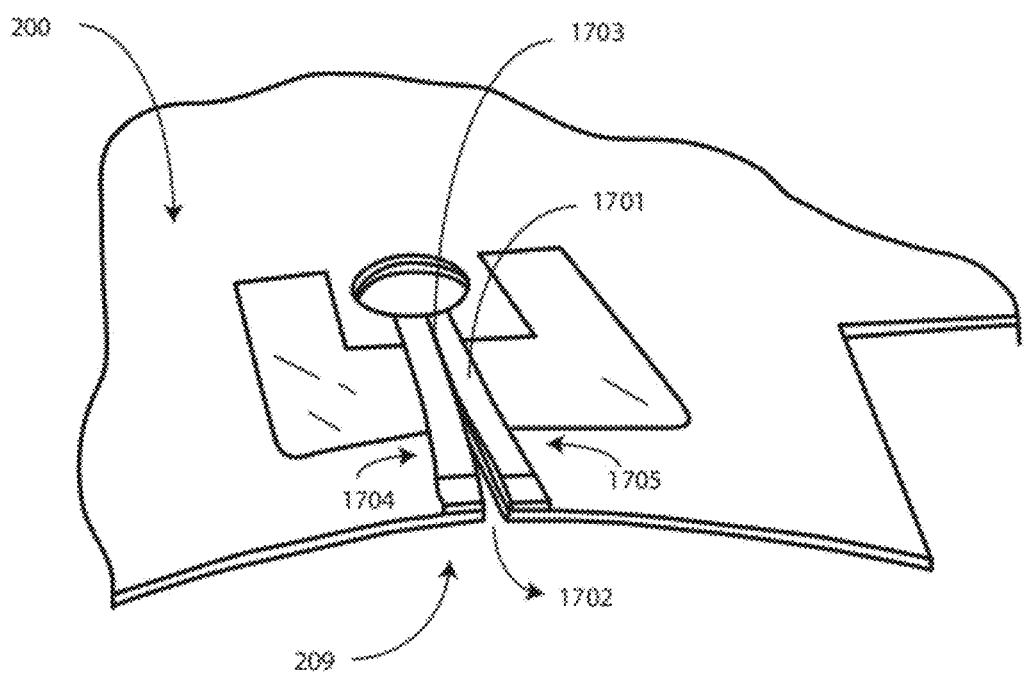
FIG. 17 illustrates one illustrative tool-less removal feature suitable for use with one or more medical drapes configured in accordance with one or more embodiments of the invention.

Turning now to FIG. 17, one of the tool-less removal features 209 is shown in more detail. As noted above, in one embodiment the tool-less removal feature 209 includes an adhesive tape strip 1701, a drape cut 1702, and a score line 1703. The adhesive tape strip 1701 generally includes a first strip side 1704 and a second strip side 1705, which are connected along the score line 1703. The score line 1703 can be formed by partially severing the adhesive tape strip 1701 along its length. Thus, the first strip side 1704 can be easily separated from the second strip side 1705 to open the drape cut 1702. In addition to securing the drape cut 1702, the adhesive tape strip 1701 seals the drape cut 1702 to prevent any violation of a sterile field formed on the patient side of the radial drape attachment 200.

Figure 18:
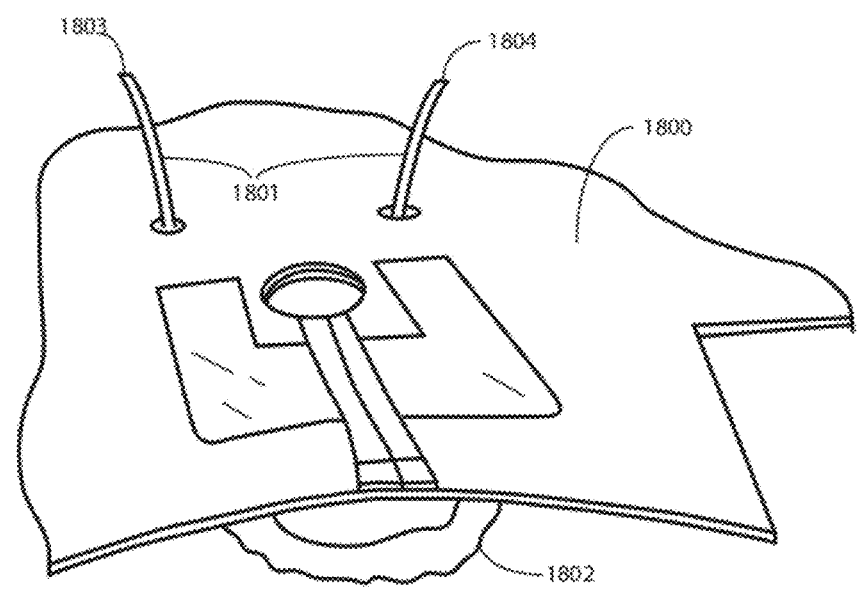
FIGS. 18 and 19 illustrate a perspective and side view, respectively, of one illustrative embedded tourniquet suitable, but optional, for use with one or more drapes configured in accordance with embodiments of the invention.
Figure 19:
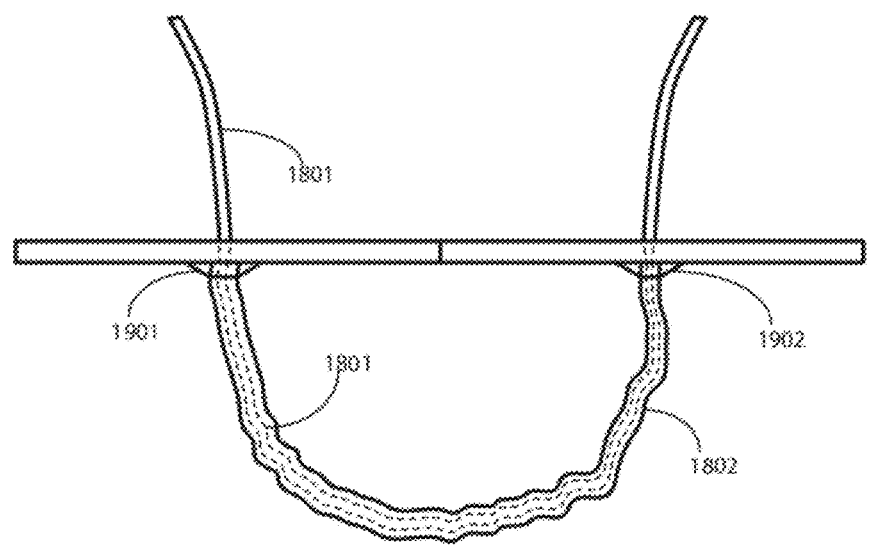

Turning now to FIGS. 18 and 19, illustrated therein is an alternate feature that may optionally be included in one or more radial drape attachments configured in accordance with embodiments of the invention. As noted above, peripherally inserted central catheter procedures frequently require tourniquets. Prior art drapes required medical personnel to fish around under an opaque drape to blindly place, apply, and release a tourniquet. FIGS. 18 and 19 illustrate a more advantageous means of accomplishing this task.

To this end, FIGS. 18 and 19 illustrate a tourniquet 1801 integrated with a radial drape attachment layer 1800. The illustrative tourniquet 1801 passes through a sleeve 1802 that is disposed on the patient side of the radial drape attachment layer 1800. Ends 1803,1804 of the tourniquet 1801 extend outwardly on the non-patient side so as to be accessible by medical personnel.

The sleeve 1802 can be integrated into the radial drape attachment layer 1800 by sealing features 1901,1902 that prevent any access to the tourniquet 1801 from the patient side of the radial drape attachment. For example, where the radial drape attachment layer 1800 is the polyethylene as described above, the sleeve 1802 can also be made from polyethylene as well, with the sealing features 1901,1902 being made from thermoplastic that is integrally formed, such as by ultrasonic sealing, with the polyethylene to prevent moisture or other materials from reaching the tourniquet 1801. This preserves the sterile field on the patient side of the radial drape attachment, while providing access to the tourniquet 1801 on the non-patient side.

When included in a radial drape attachment, the patient can slip their arm through the sleeve 1802 when being covered with the drape. The tourniquet 1801 can remain loose until needed. The tourniquet 1801 can further be easily applied and released, as needed, without the fishing and uncertainty associated with prior art systems.

Figure 20:
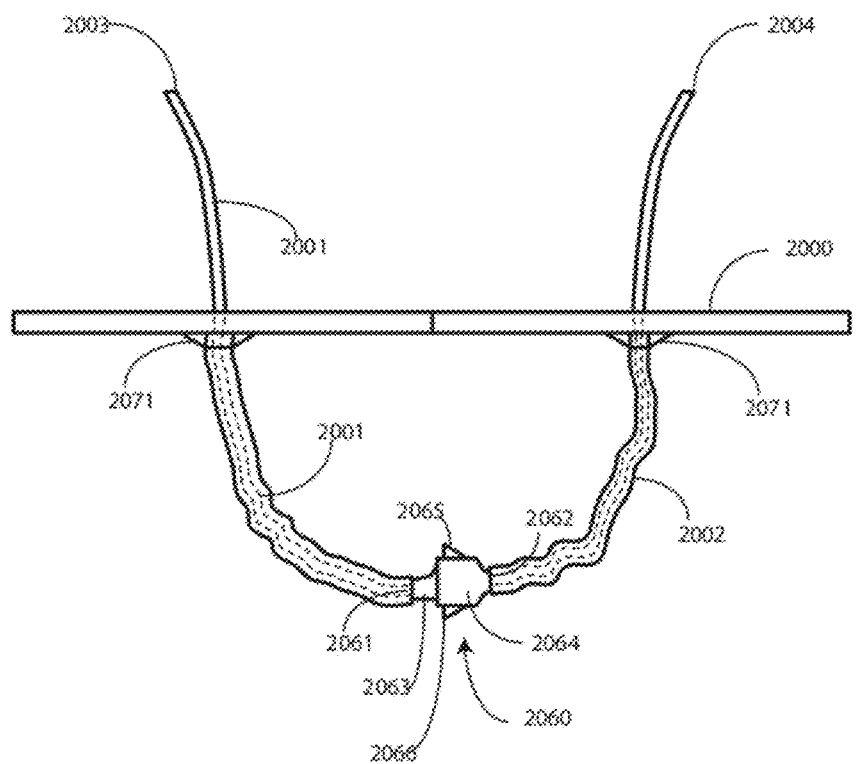
FIG. 20 illustrates another illustrative embedded tourniquet configured for optional use with one or more drapes in accordance with embodiments of the invention.

Turning now to FIG. 20, illustrated therein is another alternate feature that may optionally be included in one or more radial drape attachments configured in accordance with embodiments of the invention, where those radial drape attachments include integrated tourniquets 2001. As will be described in more detail below, one advantage of radial drape attachments configured in accordance with the present disclosure is that they can be easily used and removed by a single person. This is in contrast to prior art drapes, where two people were generally required for application to preserve the sterile field. The radial drape attachment 2000 of FIG. 20 makes the tourniquet process even simpler for a single health care services provider to use by including a coupler 2060 that bisects the tourniquet 2001. Accordingly, rather than having to fold the patient's arm back and slide it through a loop, the health care services provider is able to simply snap the coupler 2060 about the patient's limb when the radial drape attachment 2000 is being extended from the patient drape.

In the illustrative embodiment of FIG. 20, the tourniquet 2001 integrated with the radial drape attachment 2000. The tourniquet 2001 can be located in one embodiment in the transparent or pellucid portion. The tourniquet 2001 can be located along the support layer as well, which in one embodiment is opaque. The illustrative tourniquet 2001 passes through a sleeve 2002 that is disposed on the patient side of the radial drape attachment. The coupler 2060, which is disposed on the patient side of the radial drape attachment 2000, bisects the sleeve 2002. A first end 2061 of the sleeve 602 is attached to a first part 663 of the coupler 660, while a second end 662 of the sleeve 2002 is attached to a second part 2064 of the coupler 2060. In one embodiment, the coupler 2060 comprises a snap-locking device with snap features 2065 extending from the second part of the coupler 2060. Other types of couplers 2060 could also be used, including hook and latch couplers, snap couplers, buckle couplers, and so forth. Ends 2003,2004 of the tourniquet 2001 extend outwardly on the non-patient side of the radial drape attachment 2000 so as to be accessible by medical personnel. The sleeve 2002 can be integrated into the radial drape attachment 2000 by sealing features 2071,2072 that prevent any access to the tourniquet 2001 from the patient side of the radial drape attachment 2000.

Figure 21:
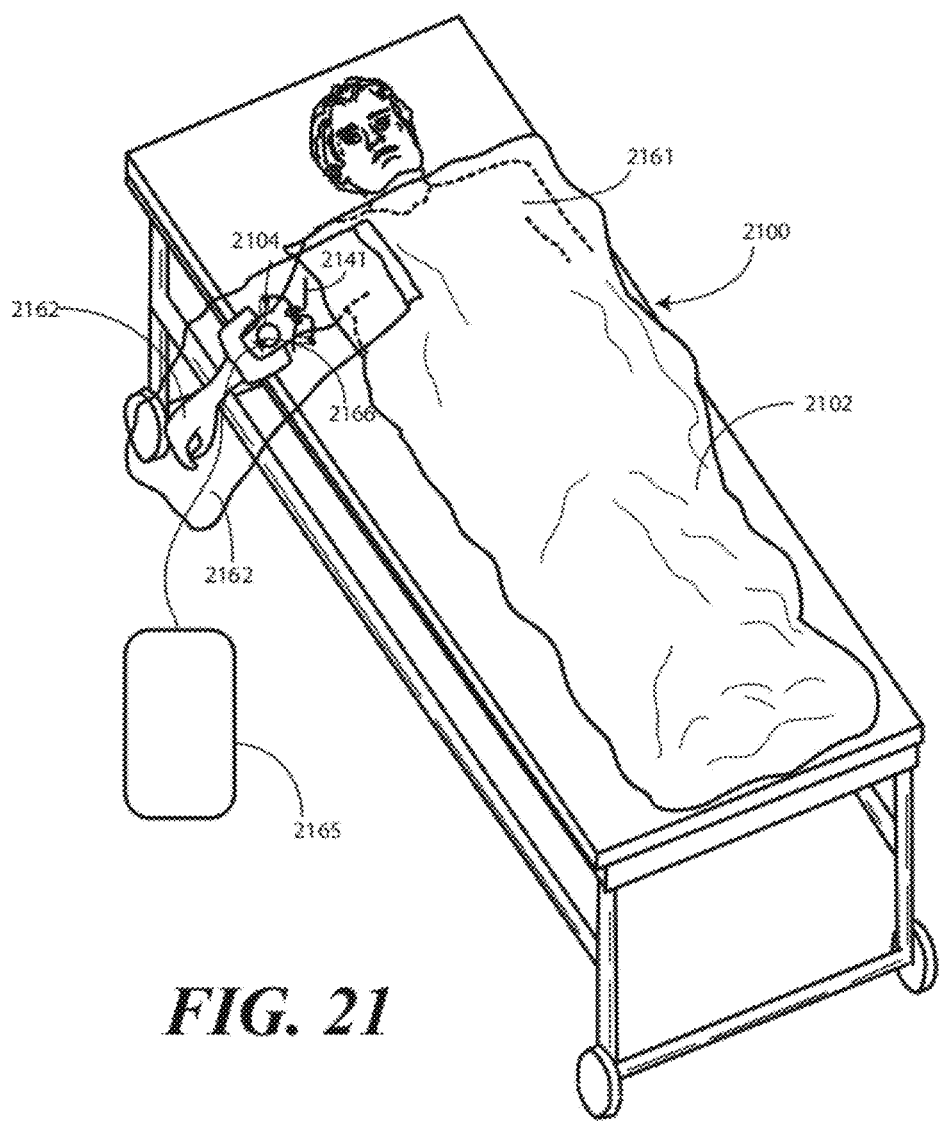
FIG. 21 illustrates one embodiment of a medical drape configured in accordance with embodiments of the invention being used during a peripherally inserted central catheter procedure.

Turning to FIG. 21, a patient 2161 is shown being covered with a medical drape 2100 configured in accordance with embodiments of the invention. The medical drape 2100 includes a radial drape attachment 2101 and a patient drape 2102. The radial drape attachment 2101 has been affixed to the patient drape 2012 by pressing the adhesive coupling 2103 against the patient drape 2102. While the radial drape attachment 2101 could be oriented at any angle relative to the patient drape 2102, and can be configured to cover any limb extending outwardly from underneath the patient drape 2102, in this illustrative embodiment it has been oriented at approximately a 90 degree relationship with the patient drape 2102 so as to cover the patient's left arm 2162, which is extended outwardly from beneath the patient drape 2102. The radial drape attachment 701 is placed over the arms 2162 of the patient 2161, with the patient drape 2102 covers the torso portions of the patient 2161.

An aperture 2104, which is configured in this illustrative embodiment as a fenestration through which a health care services provider can insert a catheter, has been placed over a peripherally inserted central catheter insertion site 2166. Accordingly, a peripherally inserted central catheter 2165 can be inserted through the aperture 2104.

This particular medical drape 2100 includes a tourniquet 2141, which has been integrated into the radial drape attachment 2101 in this illustration. The tourniquet 2141 has been tied in this embodiment by accessing ends of the tourniquet 2141 from the patient side of radial drape attachment 2101, which is also the patient side of the composite medical drape 2100. There is little or no risk of compromising the sterile field because the tourniquet 2141 passes through a sleeve that is integrated with the radial drape attachment 2101 on the patient side of the medical drape 2100.

Figure 22:
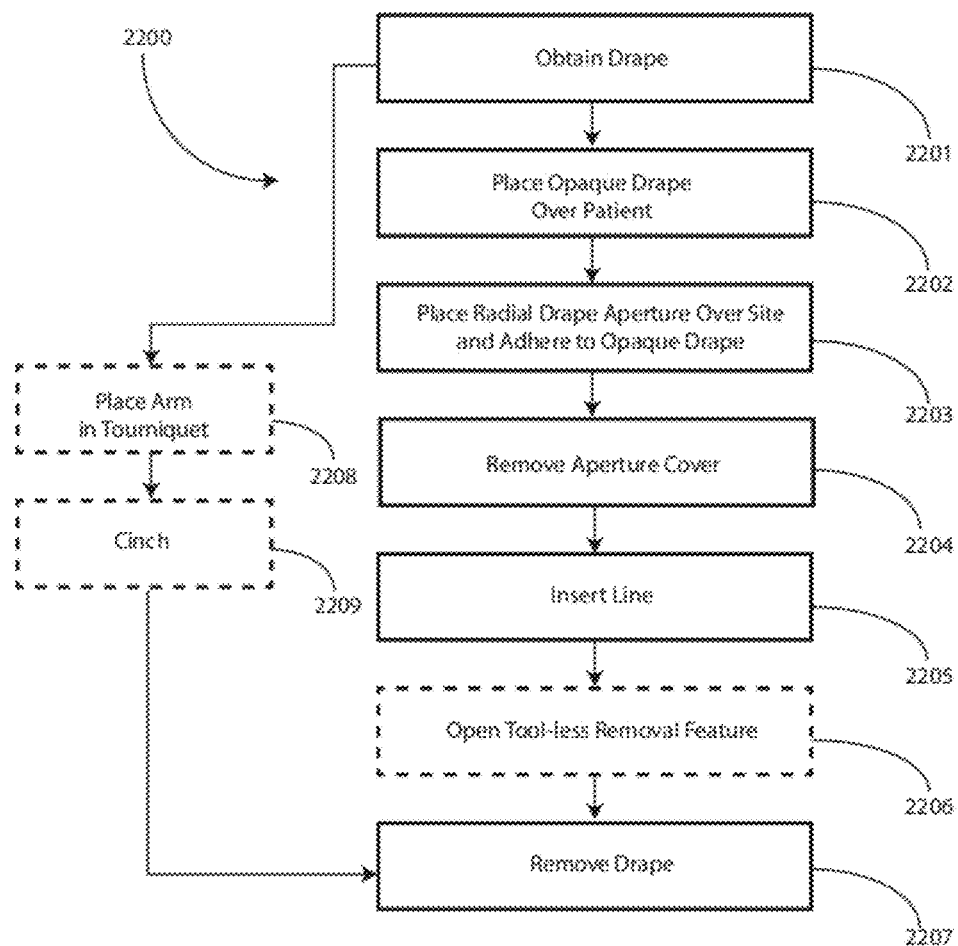
FIG. 22 illustrates a method of using medical drapes configured in accordance with one or more embodiments of the invention.

Turning to FIG. 22, a method 2200 of using medical drapes configured in accordance with embodiments of the invention is shown. The steps have largely been described above, but will be briefly recounted here.

The method 2200 begins at step 2201, where a medical practitioner or patient obtains a medical drape. In one embodiment, the medical drape is bifurcated into two components that are attachable to each other to form the medical drape. A first portion is the a patient drape. A second portion is the radial drape attachment. The radial drape attachment has an adhesive coupling with which to adhere the radial drape attachment to the patient drape.

At step 2202, the patient drape is placed across the patient. At step 2203, the radial drape attachment is placed over a limb that extends outwardly from beneath the patient drape. Once oriented at the desired radial relationship relative to the patient drape, the radial drape attachment is affixed to the patient drape at step 2203 by adhering the adhesive coupling to the patient drape such that the radial drape attachment extends beyond a perimeter of the patient drape. Step 2203 can also include placing an aperture or fenestration of the radial drape attachment over a procedure site. Where the fenestration or aperture includes a releasable cover, this can be removed at step 2204. The user or insertion specialist is then able to insert the peripherally inserted central catheter in the insertion site at step 2205.

As noted above, in one or more embodiments the radial drape attachment of the medical drape will include an integrated tourniquet. Where this is the case, optional steps for using the integrated tourniquet can be included. For example, at step 2208 the patient's arm can be placed through the integrated sleeve. Where the tourniquet includes a coupler, step 2208 can include fastening the coupler about the patient's limb. At step 2209, at the appropriate time, the insertion specialist can cinch the tourniquet disposed within the sleeve by accessing ends of the tourniquet extending from a non-patient side of the medical drape.

Once the process is complete, the medical drape is removed from the patient at step 2207. Where the radial drape attachment of the medical drape includes a tool-less removal feature, optional step 2206 can include opening the tool-less removal feature as described above.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. For example, the radial drape attachments can be configured to be opaque, while sections of the patient drape are configured to be pellucid and to define one or more apertures for central catheter insertion, such as into a vein of one of the patient's legs.

Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A medical drape, comprising:
   a patient drape;
   a radial drape attachment having an adhesive coupling configured for adhering the radial drape attachment to the patient drape such that the radial drape attachment extends beyond an outer perimeter of the patient drape.

2. The medical drape of claim 1, wherein at least some of the radial drape attachment is pellucid.

3. The medical drape of claim 2, wherein the radial drape attachment comprises at least one aperture through which a peripherally inserted central catheter can be inserted.

4. The medical drape of claim 3, wherein the at least one aperture is disposed along the at least some of the radial drape attachment.

5. The medical drape of claim 3, further comprising a tool-less removal feature extending from an edge of the radial drape attachment to the at least one aperture.

6. A method of using a drape, comprising:
   obtaining a medical drape comprising a patient drape and a radial drape attachment having an adhesive coupling with which to adhere the radial drape attachment to the patient drape; and
   affixing the adhesive coupling to the patient drape such that the radial drape attachment extends beyond an outer perimeter of the patient drape.

* * * * *